United States Patent [19]

Mercier et al.

[11] Patent Number: 4,760,189

[45] Date of Patent: Jul. 26, 1988

[54] PROCESS FOR THE PREPARATION OF DIAMINE-ALCOHOLS

[75] Inventors: Martine Mercier, Maintenon; Alain Rancurel, Mainvilliers, both of France

[73] Assignee: Laboratories Pharmascience, France

[21] Appl. No.: 903,836

[22] Filed: Sep. 3, 1986

Related U.S. Application Data

[63] Continuation of Ser. No. 683,371, Dec. 19, 1984, abandoned.

[30] Foreign Application Priority Data

Dec. 21, 1983 [FR]  France ............................. 83 20486

[51] Int. Cl.$^4$ ............................................. C07C 85/04
[52] U.S. Cl. ..................................... 564/476; 564/483; 564/503
[58] Field of Search .................... 564/476, 483, 503

[56] References Cited

U.S. PATENT DOCUMENTS 2,065,113  1/1936  Bottoms ............................ 564/476
3,432,553  3/1969  Enders et al. ..................... 564/476

FOREIGN PATENT DOCUMENTS 275622  12/1927  United Kingdom .
276012  12/1927  United Kingdom .
415691  5/1933   United Kingdom ............. 564/476

OTHER PUBLICATIONS

Wagner, R. B. & Zook, H. D., "Synthetic Organic Chemistry", Wiley & Sons, New York (1953), pp. 665–666.

Primary Examiner—Glennon H. Hollrah
Assistant Examiner—John A. Sopp
Attorney, Agent, or Firm—Handal & Morofsky

[57] ABSTRACT

The present invention relates to a new process for the preparation of diamine-alcohols.

The process according to the present invention relates to the preparation of compounds of the formula:

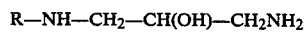

in which R is a $C_1$ to $C_{30}$ alkyl radical, characterized in that ammonia is reacted with the compound of the formula:

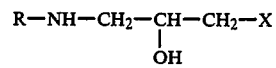

in which R has the meaning given above and X is a halogen atom.

4 Claims, No Drawings

PROCESS FOR THE PREPARATION OF DIAMINE-ALCOHOLS

This application is a continuation of application Ser. No. 683,371, filed Dec. 19, 1984, now abandoned.

The present invention relates to a process for the preparation of diamine-alcohols.

More particularly, the present invention relates to processes for the preparation of diamine-alcohols of the formula:

in which R is a $C_1$ to $C_{30}$ alkyl radical, more particularly an unbranched $C_5$ to $C_{18}$ alkyl radical.

The compounds in question are covered by the general formula of the compounds described in U.S. Pat. No. 4,196,217.

The said patent, which relates not only to diaminoalcohols but also essentially to aminoalcohol ethers, proposes a process of preparation involving a method called Gabriel's method, which proceeds via a phthalimide.

This process can be represented by the following scheme by analogy with the process described in the U.S. patent for ethers:

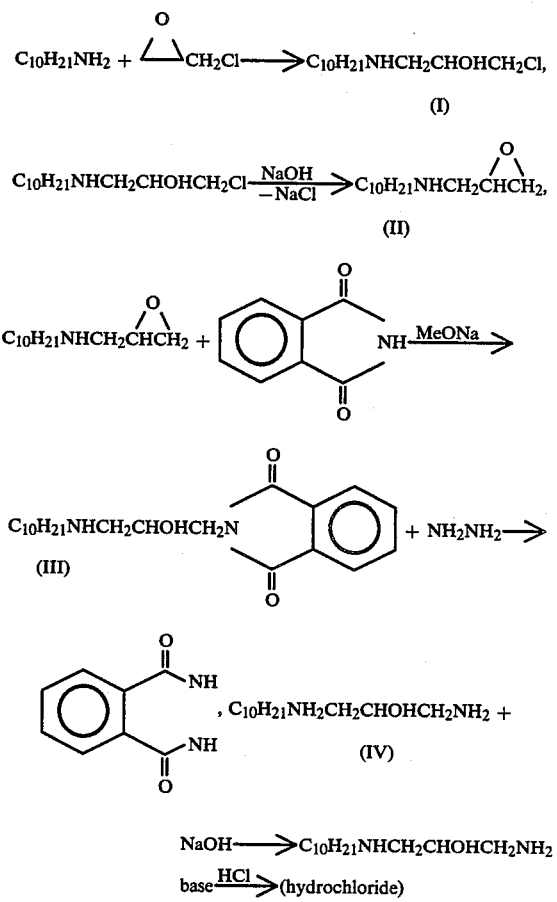

Although this process is particularly suitable for the preparation of aminoalcohol ethers when it is applied to diaminoalcohols, the yields of the process are rather low.

The overall yield of the operation for synthesizing the said aminoalcohols by the process analogous to that described in U.S. Pat. No. 4,196,217 is of the order of 35%; moreover, the purification of the products obtained is particularly difficult and is not very suitable for obtaining a product intended for use especially in the pharmaceutical industry.

It is for this reason that the present invention proposes a new process making it possible to prepare the said aminoalcohols with improved yields and under conditions which afford very pure diaminoalcohols.

The present invention relates to a process for the preparation of the said aminoalcohols of the formula:

in which R is a $C_1$ to $C_{30}$ alkyl radical, characterized in that ammonia is reacted with a compound of the formula:

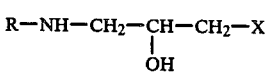

in which X is a halogen, for example chlorine, preferably under the action of heat at a temperature of between 100° and 200° C., in a solvent such as an alcohol, in particular methanol, and under pressure. This reaction can be carried out in an autoclave at a pressure of 10 to 50 bar.

The starting halogenoalcohol II is preferably prepared by reacting an amine of the formula:

with an epihalogenohydrin such as epichlorohydrin, in a solvent, in particular isopropyl alcohol or petroleum ether with a boiling range of 40°–65° C.

This reaction is preferably carried out at room temperature, in particular at a temperature below 30° C., and with an excess of the amine; thus, with one mol of amine, the yield is of the order of 50% and with a 50 mol % excess of amine, the yield increases to 80 mol %.

The final product I of the process according to the invention is isolated by any known process, especially by liquid-liquid extraction, for example using an ether, from a basic aqueous phase, the amine obtained being crystallized from the ether phase in the form of the dihydrochloride.

The yield from the amination of the compound of the formula II can be further improved by using the ammonia in the presence of a catalyst, especially an ammonium halide, in particular ammonium bromide, $NH_4Br$.

One of the advantages of the process according to the present invention is that the chlorinated derivative II is a solid which can crystallize from isopropanol, which enables the compound II to be separated off easily, and furthermore this phenomenon shifts the chemical reaction in the desired direction.

The starting compounds used in this process are known or can be prepared by known processes.

Comparative experiments for the preparation of the compound of the formula I by the process of the prior art and by the process of the invention show that the yield, which is of the order of 35% for the prior art, can reach more than 55% in the process of the invention.

The compounds of the formula I, as such or in the form of non-toxic salts, have biocidal properties, especially bactericidal properties, which make them suitable for use as antiseptics in pharmaceutical compositions or alternatively as preservatives in both pharmaceutical and cosmetic compositions or the like. These compounds can also be used by themselves or in combination for sterilizing equipment.

The examples below are intended to demonstrate other advantages and characteristics of the process according to the present invention.

EXAMPLE 1

Preparation of 3-dodecylamino-2-hydroxy-1-aminopropane 185 g of dodecylamine dissolved in 500 ml of isopropyl alcohol are introduced into a 1-liter round-bottomed flask. 93 g of freshly distilled epichlorohydrin are added dropwise, the temperature being kept below 30° C.

Stirring is maintained for 4 hours at room temperature.

The chlorinated derivative thus obtained precipitates: it is filtered off and washed with isopropanol.

Yield: 50%.

Melting point: 62° C.

30 g of a solution of methanol saturated with ammonia are introduced into a Paar bomb and 10 g of chlorinated derivative are then introduced in small portions. The bomb is closed and stirred for 4 hours at 90° C. The solution obtained is treated with 10% sodium hydroxide solution until the pH is basic. The 3-dodecylamino-2-hydroxy-1-aminopropane is then extracted with ether.

The ether phase is washed, dried over anhydrous sodium sulphate and filtered. A stream of hydrogen chloride gas is passed into the ether solution. The solution is placed in a refrigerator and the crystals of 3-dodecylamino-2-hydroxy-1-aminopropane dihydrochloride are then filtered off.

Yield: 45%.

Melting point: >270° C.

Soluble in water.

EXAMPLES 2 TO 4

If the dodecylamine is replaced respectively with decylamine, tetradecylamine and octadecylamine in the process described in Example 1, the corresponding diaminoalcohols are obtained, the characteristics of which are listed in Table I below.

EXAMPLES 5 TO 8

The compounds of Examples 1 to 4 are prepared in the form of the dihydrochloride, but it is possible to replace the hydrochloric acid with other pharmaceutically acceptable acids, especially malonic acid, maleic acid, succinic acid or methanesulphonic acid. Under these conditions, the corresponding salts are obtained, the characteristics of which are listed in Table I.

TABLE I

COMPOUNDS R—NH—CH$_2$—CH(OH)CH$_2$NH$_2$·A

| Compound of Example | R | A | M.p.° | | ELEMENTAL ANALYSIS Calculated | Found |
|---|---|---|---|---|---|---|
| 1 | C$_{10}$H$_{21}$ | 2 HCl | >270° C. | C | 51.49 | 52.72 |
| | | | | H | 10.56 | 11.01 |
| | | | | N | 9.24 | 9.27 |
| | | | | Cl | 23.43 | 23.57 |
| 2 | C$_{12}$H$_{24}$ | 2 HCl | >270° C. | N | 8.46 | 8.58 |
| | | | | Cl | 21.45 | 21.77 |
| 3 | C$_{14}$H$_{29}$ | 2 HCl | sublimed ~250° C. | N | 7.80 | 7.85 |
| | | | | Cl | 19.78 | 19.95 |
| 4 | C$_{18}$H$_{37}$ | 2 HCl | 242° C. | N | 6.75 | 6.67 |
| | | | | Cl | 17.11 | 17.39 |
| 5 | C$_{12}$H$_{24}$ | 2(CH$_2$(COOH)$_2$) | ~140° C. (soft) | C | 54.08 | 54.23 |
| | | | | H | 9.01 | 9.49 |
| | | | | N | 6.02 | 6.03 |
| 6 | C$_{12}$H$_{24}$ | 2(CH(COOH)=CH(COOH)) | 178° C. | C | 56.33 | 56.52 |
| | | | | H | 8.57 | 8.86 |
| | | | | N | 5.72 | 5.77 |
| 7 | C$_{12}$H$_{24}$ | 2(CH$_2$(COOH)CH$_2$(COOH)) | 110° C. | C | 55.87 | 56.68 |
| | | | | H | 9.31 | 9.47 |
| | | | | N | 5.67 | 5.68 |
| 8 | C$_{12}$H$_{24}$ | 2(CH$_3$SO$_3$H) | ~100° C. (soft) | C | 45.33 | 44.70 |
| | | | | H | 9.33 | 9.33 |
| | | | | N | 6.22 | 6.40 |

EXAMPLE 9

10 g of ammonium bromide, NH$_4$Br, and 50 ml of methanol saturated with ammonia are introduced into a Paar bomb and 14 g of the chlorinated derivative of Example 1 are introduced in small portions. The bomb is closed and stirred for 3 hours at 140° C.

After cooling, the methanol is evaporated off, the solution is treated with 10% sodium hydroxide solution until the pH is basic, and the diamine-alcohol is extracted with ether as described in Example 1.

This gives the title compound of Example 1 with a yield of 70%.

EXAMPLE 10

The bactericidal activity of the compounds according to the present invention was tested especially on *P. aeruginosa* and *Candida albicans.*

The results measured are listed in Table II below and compared with benzalkonium chloride.

TABLE II

| | ACTIVITY OF THE COMPOUNDS IN ppm (by the internal method) | | | |
|---|---|---|---|---|
| COMPOUND OF EXAMPLE | *PSEUDOMONAS AERUGINOSA* | | *CANDIDA ALBICANS* | |
| | Bacteriostasis | Bactericidal activity | Bacteriostasis | Bactericidal activity |
| 1 | between 100 and 250 | — | 250 | — |
| 2 | 25 | 20 | 100 | — |
| 3 | 100 | — | 50 | — |
| 4 | >500 | — | between 10 and 50 | — |
| 5 | 25 | 100 | 75 | 500 |
| 6 | 25 | 250 | 75 | 750 |
| 7 | 25 | 500 | 75 | 1000 |
| 8 | 25 | 500 | 75 | 500 |
| benzalkonium chloride | 500 | — | 10 | — |

EXAMPLE 11

The bactericidal activity of the compound of Example 2 was determined according to AFNOR Standard 72151.

Product: PVA 113.

Procedure determined after the preliminary test
1. Nature of the membranes used and reference: cellulose nitrate 0.45μ.
2. Diluent for the bacterial suspensions
Nature: tryptone salt solution
Method of preparation:

Number of washings with the diluent: 3
Volume of diluent used for each washing: 50 ml
3. Neutralizer(s) added to the counting medium and concentration: none.
4. Results of the preliminary tests under the conditions described above:

| Concentrations of the product tested | STRAIN | Control | Product |
|---|---|---|---|
| 1%. | *Pseudomonas aeruginosa* IPP A 22 | 111 | 120 |
| 1%. | *Escherichia coli* IPP 54127 | 80 | 90 |
| 1%. | *Staphylococcus aureus* ATCC9144 | 126 | 120 |
| 1%. | *Streptococcus faecalis* ITCC10541 | 82 | 75 |
| 1%. | *Mycobacterium smegmatis* IPP7326 | 127 | 140 |

5. Validity of the test:
*Pseudomonas aeruginosa:* 1%.
*E. coli:* 1%.
*Staphylococcus aureus:* 1%.
*Streptococcus faecalis:* 1%.
*Mycobacterium smegmatis:* 1%.

| | Results of the determination of the bactericidal activity | | | | | | |
|---|---|---|---|---|---|---|---|
| STRAIN | N value between 50 and 150 | X Concentration in percent (m/v) in contact with the bacteria | | | | | pH |
| | | 0.02°/₀₀ | 0.05°/₀₀ | 0.1°/₀₀ | 0.2°/₀₀ | 0.5°/₀₀ | 1°/₀₀ | |
| *Ps. aeruginosa* IPP A 22 | 85 | + | [33] | 0 | 0 | 0 | 0 | 6.1 |
| *E. coli* IPP 54127 | 128 | + | + | [131] | 1 | 0 | 0 | 6.1 |
| *St. aureus* ATCC 9144 | 102 | + | + | + | [36] | 10 | 0 | 6.0 |
| *Str. faecalis* ATCC 10541 | 119 | + | + | [86] | 0 | 0 | 0 | 6.1 |
| *M. smegmatis* IPP 7326 | 150 | + | + | + | + | + | [118] | 6.0 |

+ = more than 150 colonies
Bactericidal concentration of the product according to French Standard 72-151:

We claim:
1. A process for the preparation of a compound of the formula

$$R-NH-CH_2-CH(OH)-CH_2NH_2$$

comprising the steps of:
(1) reacting an epihalogenohydrin with an excess of an amine of the formula

R—NH$_2$ in a solvent to form a reaction product having the formula

R—NH—CH$_2$—CH(OH)—CH$_2$—X and (2) reacting the product of step (1) with ammonia at a temperature of about 100° C. to 200° C. in an alcohol solvent and under a pressure of 10-50 bar.; wherein R is a C$_1$ to C$_{30}$ alkyl radical, and X is a halogen.

2. The process of claim 1, wherein the reaction is carried out in isopropanol or petroleum ether.

3. The process according to claim 1, characterized in that the alcohol solvent is methanol.

4. The process according to claim 1 characterized in that the reaction of step (2) is carried out in the presence of a quaternary ammonium halide catalyst.

* * * * *

UNITED STATES PATENT AND TRADEMARK OFFICE
CERTIFICATE OF CORRECTION

PATENT NO. : 4,760,189
DATED : July 26, 1988
INVENTOR(S) : Martine Mercier et al It is certified that error appears in the above-identified patent and that said Letters Patent is hereby corrected as shown below:

On the title page assignee should read

--(73) Assignee: Laboratoires Pharmascience --.

Signed and Sealed this

Seventeenth Day of January, 1989

Attest:

DONALD J. QUIGG

*Attesting Officer*  *Commissioner of Patents and Trademarks*